United States Patent
Funazaki et al.

(10) Patent No.: US 9,355,918 B2
(45) Date of Patent: May 31, 2016

(54) METHOD FOR PRODUCING HIGH-PURITY POLYCRYSTALLINE SILICON

(71) Applicant: Shin-Etsu Chemical Co., Ltd., Tokyo (JP)

(72) Inventors: Kazunori Funazaki, Niigata (JP); Kazuomi Sato, Niigata (JP); Shuichi Miyao, Niigata (JP)

(73) Assignee: SHIN-ETSU CHEMICAL CO., LTD., Chiyoda-ku (JP)

( * ) Notice: Subject to any disclaimer, the term of this patent is extended or adjusted under 35 U.S.C. 154(b) by 15 days.

(21) Appl. No.: 14/407,255

(22) PCT Filed: Jun. 13, 2013

(86) PCT No.: PCT/JP2013/003729
§ 371 (c)(1),
(2) Date: Dec. 11, 2014

(87) PCT Pub. No.: WO2013/187070
PCT Pub. Date: Dec. 19, 2013

(65) Prior Publication Data
US 2015/0170976 A1 Jun. 18, 2015

(30) Foreign Application Priority Data
Jun. 14, 2012 (JP) .................. 2012-134863

(51) Int. Cl.
*G01R 31/26* (2014.01)
*H01L 21/66* (2006.01)
(Continued)

(52) U.S. Cl.
CPC ............... *H01L 22/10* (2013.01); *C01B 33/03* (2013.01); *C01B 33/035* (2013.01); *G01N 33/00* (2013.01);
(Continued)

(58) Field of Classification Search
CPC ................... H01L 21/02532; H01L 21/02595; H01L 21/0262; H01L 22/10
USPC ......................................................... 438/14
See application file for complete search history.

(56) References Cited

U.S. PATENT DOCUMENTS 4,409,195 A  10/1983  Darnell et al.
4,526,769 A  7/1985  Ingle et al.
(Continued)

FOREIGN PATENT DOCUMENTS

CN  101531674 A  9/2009
CN  102143909 A  8/2011
(Continued)

OTHER PUBLICATIONS

Combined Office Action and Search Report issued Nov. 2, 2015 in Chinese Patent Application No. 201380031327.9 (with English translation of category of cited documents).
(Continued)

*Primary Examiner* — Long K Tran
(74) *Attorney, Agent, or Firm* — Oblon, McClelland, Maier & Neustadt, L.L.P.

(57) ABSTRACT

The present invention provides technology for realizing higher purification of a polycrystalline silicon. First, trichlorosilane is prepared as a sample (S101) and then the carbon-containing impurities content in the trichlorosilane is analyzed by GC/MS-SIM method (S102). The quality of the trichlorosilane is determined based on the analysis results (S103) and the trichlorosilane determined to be a good material (S103: Yes) is used as the raw material for producing a high-purity polycrystalline silicon by CVD method (104). In case, the trichlorosilane determined to be a bad material (S103: No) is not used as the raw material for producing a polycrystalline silicon. When the impurities analysis by GC/MS-SIM method is performed using, as a separation column, a column having a non-polar column and a medium-polar column connected in series with each other, it is possible to simultaneously perform both of the separation of chlorosilanes and hydrocarbons and the separation of chlorosilanes and methylsilanes.

6 Claims, 20 Drawing Sheets

(51) Int. Cl.
  *C01B 33/03* (2006.01)
  *C01B 33/035* (2006.01)
  *G01N 33/00* (2006.01)
  *H01L 21/02* (2006.01)

(52) U.S. Cl.
  CPC ...... *H01L 21/0262* (2013.01); *H01L 21/02532* (2013.01); *H01L 21/02595* (2013.01); *G01N 2033/0095* (2013.01)

(56) References Cited

U.S. PATENT DOCUMENTS

| | | | |
|---|---|---|---|
| 4,986,971 A | | 1/1991 | Forwald et al. |
| 7,790,132 B2 | | 9/2010 | Shimizu et al. |
| 2007/0073075 A1 | * | 3/2007 | Paetzold et al. ............... 556/466 |
| 2009/0068081 A1 | | 3/2009 | Uehara et al. |
| 2010/0233612 A1 | * | 9/2010 | Uemura et al. ............ 430/111.1 |
| 2011/0142742 A1 | | 6/2011 | Hayashida et al. |
| 2011/0158885 A1 | | 6/2011 | Hayashida et al. |
| 2013/0001063 A1 | | 1/2013 | Tanaka et al. |

FOREIGN PATENT DOCUMENTS

| | | |
|---|---|---|
| CN | 102286016 A | 12/2011 |
| CN | 102351195 A | 2/2012 |
| JP | 56-073617 A | 6/1981 |
| JP | 60-036318 A | 2/1985 |
| JP | 02-208217 A | 8/1990 |
| JP | 09-169514 A | 6/1997 |
| JP | 10-029813 A | 2/1998 |
| JP | 11-049509 A | 2/1999 |
| JP | 2003-172726 A | 6/2003 |
| JP | 2004-149351 A | 5/2004 |
| JP | 2009-062212 A | 3/2009 |
| JP | 2009-062213 A | 3/2009 |
| JP | 2010-281699 A | 12/2010 |
| JP | 2011-184255 A | 9/2011 |
| WO | 2010/021339 A1 | 2/2010 |

OTHER PUBLICATIONS

Extended European Search Report issued Oct. 8, 2015 in Patent Application No. 13804452.4.

International Search Report issued Sep. 24, 2013 in PCT/JP2013/003729 filed Jun. 13, 2013.

Harry Prest, et al., "New Approaches to the Development of GC/MS Selected Ion Monitoring Acquisition and Quantitation Methods" Agilent Technologies, Nov. 14, 2001, 6 Pages.

* cited by examiner

METHOD FOR PRODUCING HIGH-PURITY POLYCRYSTALLINE SILICON

TECHNICAL FIELD

The present invention relates to a technology for producing a high-purity polycrystalline silicon. More specifically, the present invention relates to a technology for realizing the higher purification of a polycrystalline silicon by using a raw material gas having a low concentration of carbon-containing impurities.

BACKGROUND ART

A high-purity polycrystalline silicon of a semiconductor grade is usually produced by CVD method called "Siemens method" using chlorosilanes gas mainly composed of trichlorosilane in the presence of hydrogen as a raw material (refer to, for example, Patent Literature 1: Japanese Patent Laid-Open No. 56-73617).

In general, chlorosilanes for manufacturing a polycrystalline silicon are synthesized by the reaction of a metallurgical grade silicon with hydrogen chloride (refer to, for example, Patent Literature 2: Japanese Patent Laid-Open No. 2-208217 and Patent Literature 3: Japanese Patent Laid-Open No. 9-169514) or the reduction of tetrachlorosilane by hydrogen (refer to, for example, Patent Literature 4: Japanese Patent Laid-Open No. 60-36318 and Patent Literature 5: Japanese Patent Laid-Open No. 10-29813).

However, since the synthesized chlorosilanes contain impurities derived from the metallurgical grade silicon, etc. used as a raw material, the synthesized chlorosilanes, after having been subjected to a chemical treatment for high purification (refer to, for example, Patent Literature 6: Japanese Patent Laid-Open No. 2009-62213) or a high precision distillation, is used as a raw material for producing a polycrystalline silicon.

These high purifications (i.e., the removal of impurities) are critically important especially in a polycrystalline silicon of a semiconductor grade. This is because, in case of the impurities contained being phosphorus or arsenic serving as a donor in a silicon crystal, or boron or aluminum serving as an acceptor in a silicon crystal, the impurities significantly affect the electrical properties (resistivity) of a polycrystalline silicon when incorporated thereinto even at a trace amount. Thus, the donor and acceptor impurities contained in chlorosilanes as a raw material are removed by various methods (for example, chemical treatments as described in Patent Literature 6).

Further, carbon impurities form, in a silicon crystal, an impurity level in the band gap to act as a carrier trap, or accelerate the formation of precipitation nuclei of oxygen in the crystal to induce crystal defects during the process of manufacturing a semiconductor device. Therefore, the content of carbon impurities also becomes problematic in a polycrystalline silicon of a semiconductor grade.

As one of the causes of the contamination of carbon impurities into a polycrystalline silicon, carbon-containing impurities such as alkyl chlorosilanes and hydrocarbons can be considered which are generated during the production of trichlorosilane and which are mixed into trichlorosilane or hydrogen. These carbon-containing impurities may be some times mixed into at about several tens of ppm by weight ratio when producing trichlorosilane.

In particular, methyldichlorosilane, which is the main component of methylchlorosilanes, has a boiling point (41° C.) close to that (32° C.) of trichlorosilane which is the subject of a distillation purification, and its removal is therefore difficult. For this reason, a number of methods for removing methyldichlorosilane have been proposed (for example, Patent Literatures 7-9).

CITATION LIST

Patent Literature

Patent Literature 1: Japanese Patent Laid-Open No. 56-73617
Patent Literature 2: Japanese Patent Laid-Open No. 2-208217
Patent Literature 3: Japanese Patent Laid-Open No. 9-169514
Patent Literature 4: Japanese Patent Laid-Open No. 60-36318
Patent Literature 5: Japanese Patent Laid-Open No. 10-29813
Patent Literature 6: Japanese Patent Laid-Open No. 2009-62213
Patent Literature 7: Japanese Patent Laid-Open No. 2004-149351
Patent Literature 8: Japanese Patent Laid-Open No. 2011-184255
Patent Literature 9: Japanese Patent Laid-Open No. 2009-62212
Patent Literature 10: Japanese Patent Laid-Open No. 11-49509

Non Patent Literature

Non Patent Literature 1: New Approaches to the Development of GC/MS Selected Ion Monitoring Acquisition and Quantitation Methods Nov. 14, 2001, 5988-4188EN Agilent Technologies, Inc. (Technical Reference)

SUMMARY OF INVENTION

Technical Problem

According to Japanese Patent Laid-Open No. 11-49509 (Patent Literature 10), if carbon impurities are brought in the form of methylchlorosilanes into the generation reaction system of a polycrystalline silicon, the carbon impurities are not incorporated directly into the polycrystalline silicon at so high rate, but easy to be contained and stored in the reaction system as methane and, as a result, may deteriorate the quality of the resultant polycrystalline silicon.

Therefore, in order to produce a high-purity polycrystalline silicon, it is necessary to reduce as much as possible the amount of carbon impurities in the chlorosilanes to be supplied as a raw material.

To that end, measurement of the amount of carbon impurities contained in chlorosilanes in advance is needed, and, in the analysis for that, GC-FID method (gas chromatography/hydrogen ionization detector) has been typically used hitherto.

GC-FID method has been used particularly as a standard high-sensitivity analytical method for analyzing methyldichlorosilane which is a main carbon impurity in trichlorosilane, but the detection limit is about 0.1 ppmw for general organic compounds, and about 0.1 ppmw for methylsilanes.

An FID detector (hydrogen ionization detector) uses combustion by oxyhydrogen gas for the detection of components, and therefore the detection sensitivity is destabilized due to $SiO_2$ generated in the detection part, resulting in a problem that the continuous use is difficult.

Furthermore, there is a method in which a carrier gas is switched, for preventing the generation of a large amount of $SiO_2$, by a rotary valve after the separation of trichlorosilane as the main component, thereby not introducing the component into the FID detector. In that method, however, shock at the time of switching a rotary valve causes baseline drift or affects the chromatographic shape of component peaks, resulting also in a problem that it is difficult to perform a quantitative analysis of a trace amount with high accuracy.

In addition to these problems, there is no column available which can simultaneously perform both of the separation of chlorosilanes and hydrocarbons and the separation of chlorosilanes and methylsilanes, when impurities in trichlorosilane are to be analyzed by GC-FID method. Therefore, the analyses are needed to be performed depending on individual separation conditions, resulting also in a problem that the analytical work must be performed separately twice.

Thus, there has been a need for more highly purifying a polycrystalline silicon of a semiconductor grade, but the conventional approaches have not fully met this need under the present circumstances.

The present invention has been made in view of these problems, and an object of the present invention is to provide a technology for realizing higher purification of a polycrystalline silicon by using a raw material gas having a low concentration of carbon-containing impurities.

Solution to Problem

In order to solve the above problems, a method for producing a high-purity polycrystalline silicon according to the present invention is to produce a high-purity polycrystalline silicon using chlorosilanes by CVD method, and is characterized by performing a quality determination by analyzing the content of carbon-containing impurities including methyldichlorosilane and isopentane by GC/MS-SIM method, and using, as the chlorosilanes, trichlorosilane satisfying conditions which are quality determination criteria set based on permissible values of the content of carbon-containing impurities whose values are provided on the basis of a permissible value of the content of carbon in an objective polycrystalline silicon.

More conveniently, the carbon-containing impurities to be analyzed by the GC/MS-SIM method are methyldichlorosilane and isopentane.

Preferably, the quality determination criteria are that methylsilanes as the carbon-containing impurities are 0.01 ppmw or lower, and hydrocarbons as the carbon-containing impurities are 0.05 ppmw or lower.

Furthermore, preferably, the analysis of the impurities by the GC/MS-SIM method separates the components using, as a separation column, a column having a non-polar column and a medium-polar column connected in series with each other.

Advantageous Effects of Invention

According to the method for producing a polycrystalline silicon of the present invention, chlorosilanes whose content of carbon-containing impurities exceeds the quality determination criteria are excluded from the raw material, and higher purification of a polycrystalline silicon can be therefore achieved.

By using, as a separation column, a column having a non-polar column and a medium-polar column connected in series with each other, both of the separation of chlorosilanes and hydrocarbons and the separation of chlorosilanes and methylsilanes can be simultaneously performed according to GC/MS-SIM method.

DESCRIPTION OF EMBODIMENTS

Figure 1:
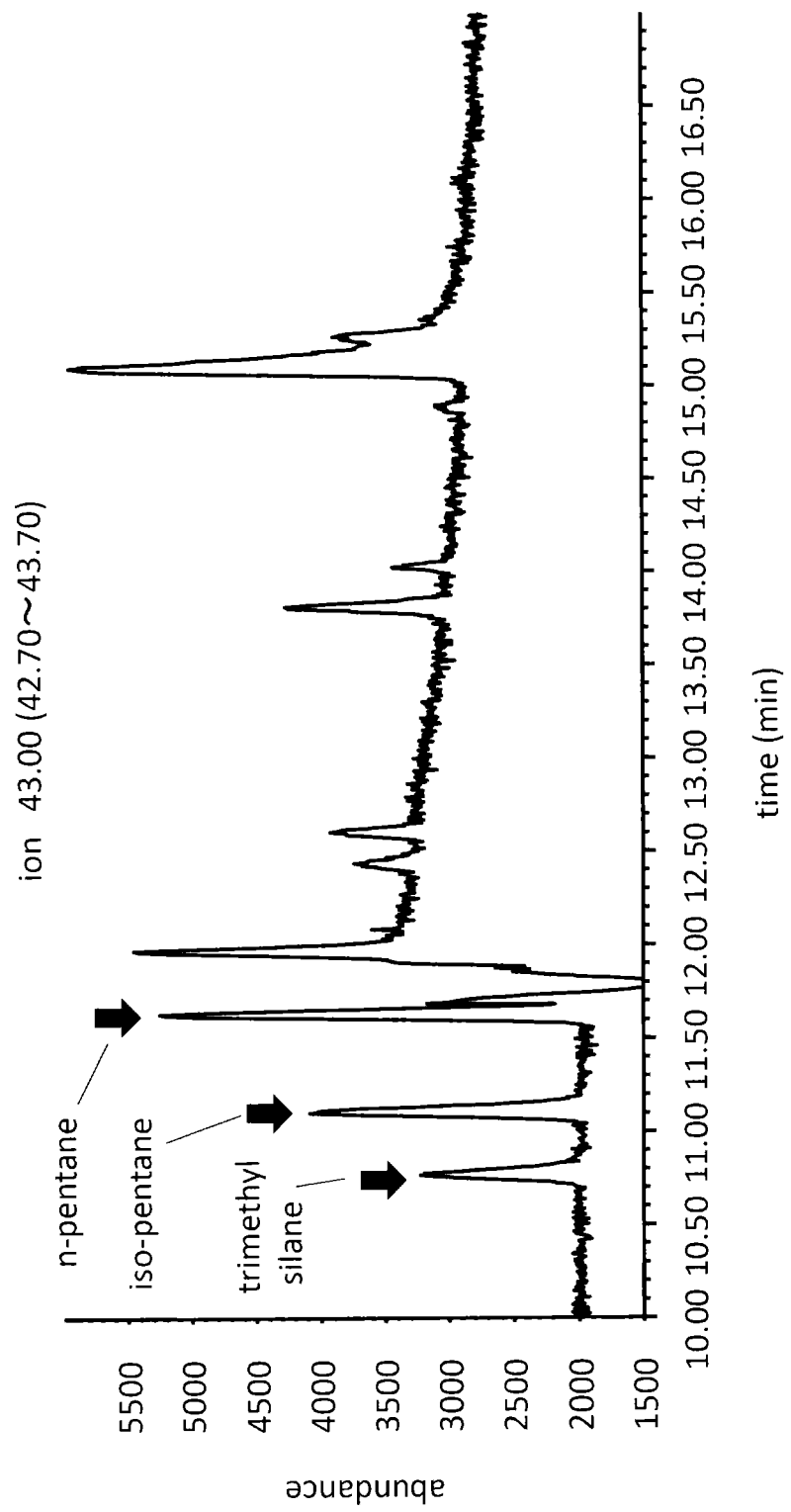
FIG. 1 is a chart (measurement chart of mass number of 43) obtained by GC/MS-SIM analysis of Sample A.

In the following, a method for producing a polycrystalline silicon according to the present invention will be described in detail with reference to the accompanying drawings.

As described above, many proposals and industrializations have been already made for a method of synthesizing trichlorosilane with high purity by a distillation separation of chlorosilanes. Chlorosilanes may be obtained by, for example, a direct method using a metallurgical grade silicon and hydrogen chloride (refer to Patent Literatures 2 and 3). When a polycrystalline silicon is produced using, as a raw material, tetrachlorosilane or trichlorosilane which is a by-product in obtaining chlorosilanes by the direct method, tetrachlorosilane is also obtained from an exhaust gas generated in the direct method, and the reduction of the tetrachlorosilane by reacting with hydrogen in the presence of a metallurgical grade silicon may also produce chlorosilanes (refer to Patent Literatures 4 and 5).

Then, after obtaining trichlorosilane fractions by distillation separation of the produced chlorosilanes, the fractions are subjected to a chemical treatment (refer to Patent Literature 6), etc. to remove impurities that become acceptors or donors such as boron or phosphorus, followed by a precision distillation to obtain a high-purity trichlorosilane.

GC-FID method is generally used to measure impurities in the obtained trichlorosilane, but if the purification process of trichlorosilane is appropriate, the content of the impurities contained is the lower detection limit of GC-FID method or lower, specifically, is 0.1 ppmw or lower for general organic compounds, and 0.1 ppmw or lower for methylsilanes.

However, impurities of which content is these values or lower cannot be detected by GC-FID method, and such impurities may be therefore obstacles in realizing the higher purification of a polycrystalline silicon.

Thus, the present inventors have investigated a method for detecting carbon-containing impurities in trichlorosilane with high sensitivity and, as a result, found that use of GC/MS-SIM method can increase the detection sensitivity of the carbon-containing impurities by about 10-fold as compared to GC-FID method, to lead to the completion of the present invention. Here, GC/MS refers to a gas chromatograph mass spectrometer, and SIM refers to selected ion monitoring.

By using GC/MS-SIM method, the lower detection limit of carbon-containing impurities in trichlorosilane becomes 0.01 ppmw for methylsilanes, and 0.05 ppmw for general carbon-containing compounds, which enables an analysis with sensitivity of about 10-fold as compared to GC-FID method. That is, the analysis of carbon-containing impurities in trichlorosilane according to GC/MS-SIM method makes it possible to produce a polycrystalline silicon using, as a raw material, trichlorosilane guaranteed with 0.01 ppmw or lower for methylsilanes, and 0.05 ppmw or lower for general carbon-containing compounds (hydrocarbons).

This is because the rate at which the carbon-containing impurities as described above is transferred as carbon into the produced polycrystalline silicon, namely the transfer rate, has been found to be in the range of about 1-10% from the results of investigations according to the present inventors.

In this range, even if the production of a polycrystalline silicon is performed in an environment where the maximum amount of the impurities is transferred, when trichlorosilane is selected as a raw material based on quality determination criteria of 0.01 ppmw or lower and 0.05 ppmw or lower, respectively, for the contents of methyldichlorosilane and isopentane which are likely to be mixed into the product even when highly purified, it can be assumed that methyldichlorosilane and isopentane are individually transferred as carbon of 10% of the total amount, resulting in the concentration of carbon in the synthesized polycrystalline silicon of 0.048 ppma or lower.

That is, use of that criteria enable the production of a high-purity polycrystalline silicon containing carbon of lower than 0.05 ppma of the lower quantification limit of a cryogenic FT-IR method which has at present the highest sensitivity when measuring the concentration of carbon in a single crystal silicon.

Here, describing the basis for the above carbon concentration of "0.048 ppma", when isopentane in trichlorosilane is 0.05 ppmw, the carbon content becomes $0.05 \times (12 \times 5)/72 = 0.042$ ppmw, and the carbon content of trichlorosilane therefore becomes $C(ppma) = (0.042 \times 135.45)/12.0 = 0.47$.

Here, the above 135.45 is the molecular weight of trichlorosilane, the above 12.0 is the atomic weight of C.

Similarly, when $CH_3$—$SiH$—$Cl_2$ in trichlorosilane is 0.01 ppmw, the carbon content becomes $0.01 \times (12 \times 1)/114 = 0.0011$ ppmw, and the carbon content in trichlorosilane therefore becomes $C(ppma) = (0.0011 \times 135.45)/12.0 = 0.012$.

In addition, from the results of the investigation according to the present inventors, the actual transfer rate is 1 to 10% and, when calculated with 10% of the maximum value, the content of carbon transferred to (incorporated into) the synthesized polycrystalline silicon becomes $0.047 + 0.0012 = 0.048$ ppma.

That is, a method for producing a high-purity polycrystalline silicon according to the present invention is to produce a high-purity polycrystalline silicon using chlorosilanes by CVD method, and uses, as a raw material, trichlorosilane which is subjected to a quality determination by analyzing the content of the carbon-containing impurities by GC/MS-SIM method and which satisfies conditions of quality determination criteria.

The quality determination criteria are that methylsilanes as the carbon-containing impurities are 0.01 ppmw or lower, and hydrocarbons as the carbon-containing impurities are 0.05 ppmw or lower, for the reasons as described above.

The procedures of a quantitative analysis by GC/MS-SIM method are introduced by Non-Patent Literature 1, etc., and conditions for the analysis of carbon-containing impurities in trichlorosilane in the present invention are, for example, described in the following.

For the gas chromatography conditions, ordinary analysis conditions for chlorosilanes may be applied as they are and, for example, hydrogen, helium, nitrogen, etc. are used as a carrier gas.

As the separation column, a medium-polar capillary column is preferred for methylsilanes, and a non-polar capillary column is preferred for hydrocarbons. In a preferred aspect of the present invention, a column having a non-polar column and a medium-polar column e connected in series with each other is used. By using such a column, both of the separation of chlorosilanes and hydrocarbons and the separation of chlorosilanes and methylsilanes can be simultaneously performed by GC/MS-SIM method.

There are no particular limitations on the non-polar column and medium-polar column, and the known columns may be appropriately selected and used. Such columns include products from Agilent Technologies, Inc., Varian Inc., Supelco, Inc., Restek Corp., and GL Sciences, Inc.

As the commercially available non-polar capillary column, DB-1, DB-5, VF-1, VF-5, SPB-1, SPB-5, Rtx-1, Rtx-5, TC-1, TC-5, etc. may be suitably used.

As the commercially available medium-polar capillary column, DB-17, DB-200, DB-210, DB-225, VF-17, VF-23, VF-200, VF-1701, Select Silane, SBP-17, SP-2331, Rtx-225, Rtx-1701, TC-17, etc. may be suitably used.

An oven temperature in performing the separation is in the range of about 20 to 150° C., and assembling a heating program in this temperature range may obtain a good separation.

As an ionization method for MS, an electron impact ionization method (EI) may be adopted and, for example, gas molecule may be changed into a positive monovalent ion by applying thereto an electron beam bombardment of 70 eV. In this case, the ionization current of about 34 to 35 μA, the ionization chamber temperature of 200 to 250° C., the transfer line temperature of 200 to 250° C. and the detector voltage of 1000 to 2000 V may be made as guides.

Further, analysis results with high accuracy may be obtained by setting monitor ions in the SIM (m/z) in detection order, as follows: isopentane (m/z=43, m/z=57, m/z=72), n-pentane (m/z=43, m/z=57, m/z=72), tetramethylsilane (m/z=43, m/z=45, m/z=73), dimethylchlorosilane (m/z=59, m/z=79, m/z=93), methyldichlorosilane as the main impurities (m/z=79, m/z=99, m/z=113), trimethylchlorosilane (m/z=65, m/z=73, m/z=93), methyltrichlorosilane (m/z=148, m/z=113, m/z=133), and dimethyldichlorosilane (m/z=128, m/z=93, m/z=113), and setting a cycle time of 4.0-5.0 cycles/sec.

In the present invention, when producing a high-purity polycrystalline silicon using trichlorosilane as a raw material by CVD method, more specifically, by Siemens method, the content of carbon-containing impurities in the trichlorosilane are in advance analyzed by GC/MS-SIM method to determine the trichlorosilane satisfying the conditions of quality determination criteria as a good material, and this good material determined is used as the raw material.

The method for producing a polycrystalline silicon by Siemens method is widely known and, for example, is performed as described in the following.

First, a silicon core which will become a seed crystal for a polycrystalline silicon is placed in CVD reactor, followed by energization for heating the silicon core. Further, while maintaining the surface temperature of the silicon core at 900 to 1200° C., trichlorosilane which has been determined as a good material by GC/MS-SIM method is supplied together with hydrogen as a carrier gas. The trichlorosilane is decomposed on the silicon core, and a polycrystalline silicon is grown on the silicon core.

At this time, chlorosilanes such as unreacted trichlorosilane and tetrachlorosilane are discharged together with hydrogen as exhaust gases, and the hydrogen and trichlorosilane may be recovered and reused. In addition, chlorosilanes such as tetrachlorosilane are converted into trichlorosilane and reused (refer to Patent Literatures 4 and 5).

According to the present invention, use of GC/MS-SIM method can increase the detection sensitivity of carbon-containing impurities by about 10-fold as compared to that obtained using conventional GC-FID method, and the purity of trichlorosilane, which is a raw material for producing a polycrystalline silicon, can be therefore easily increased and, as a result, the higher purification of a polycrystalline silicon can be achieved.

Examples

The present invention will be specifically described below with reference to examples.

[Confirmation of Detection Peaks of Chlorosilanes]

Sample A which contained 2 ppmw of each of supposed impurities and which was for trichlorosilane GC analysis was prepared as a highly purified trichlorosilane, and analyzed under the following conditions.

Figure 2:
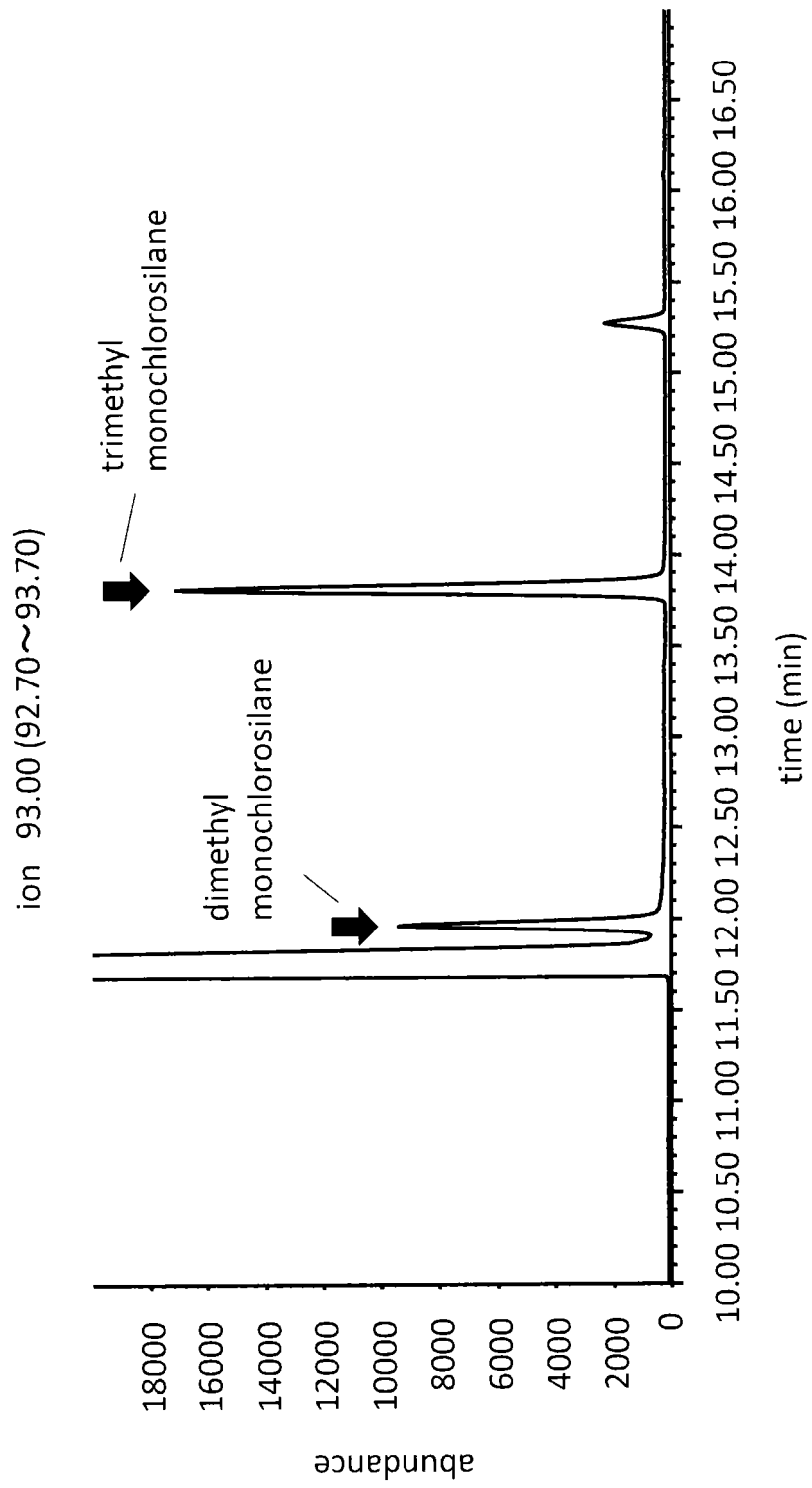
FIG. 2 is a chart (measurement chart of mass number of 93) obtained by GC/MS-SIM analysis of Sample A.
Figure 3:
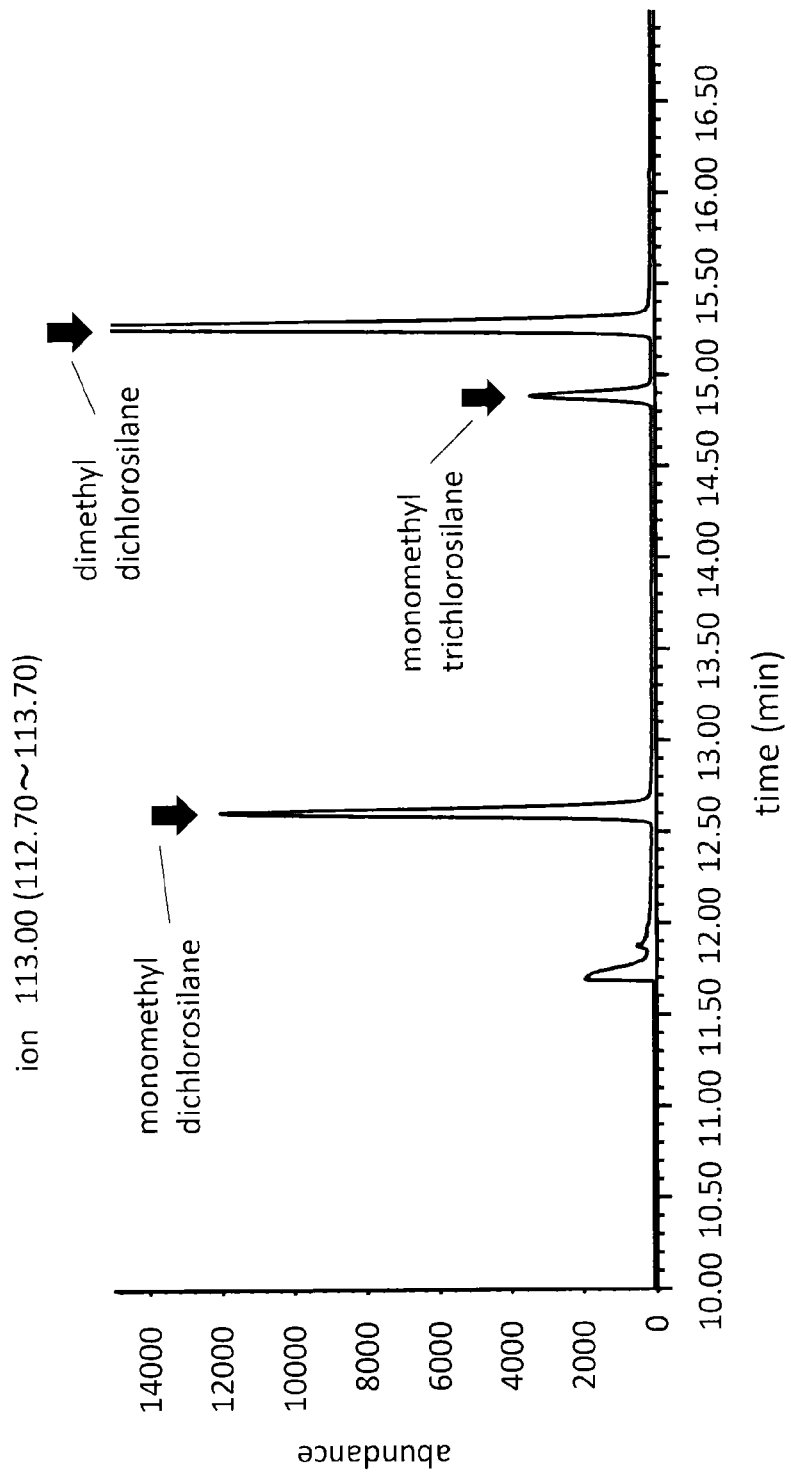
FIG. 3 is a chart (measurement chart of mass number of 113) obtained by GC/MS-SIM analysis of Sample A.

GC Conditions:
Carrier gas: He (1 ml/min)
Column: VF-200 manufactured by Varian Inc. was further connected in series with the outlet side of DB-1 manufactured by Agilent Technologies, Inc. and used as a column
Injection: Split (0.6 μL), 23.4 psi, 150° C.
Oven temperature: 20 to 150° C. (The temperature was increased at a rate of 10° C./min, and maintained at 150° C.)
GC/MS-SIM Detection Conditions:
Ionization energy: 70 eV
Ionization current: 34 μA
Ion source temperature: 230° C.
Transfer line temperature: 230° C.
Detector voltage: 1000 to 2000 V
Monitor ions: isopentane, n-pentane, tetramethylsilane, dimethyl monochlorosilane, trimethyl monochlorosilane, methyltrichlorosilane, dimethyldichlorosilane
Cycle time: 4.3 cycles/sec.
Result:

Charts obtained by the GC/MS-SIM analysis described above are shown in FIGS. 1 to 3. FIG. 1 is a measurement chart of mass number of 43, FIG. 2 is a measurement chart of mass number of 93, and FIG. 3 is a measurement chart of mass number of 113. It was confirmed that the measurements of mass numbers of 43, 93 and 113 in GC/MS-SIM method enabled, by comparing with each of the gas chromatography charts previously obtained by GC-FID method, the detections of peaks derived from trimethylsilane, isopentane and n-pentane; the detections of peaks derived from dimethyl monochlorosilane and trimethyl monochlorosilane; and the detections of peaks derived from monomethyldichlorosilane, monomethyltrichlorosilane and dimethyldichlorosilane, respectively.

[Confirmation of the Detection Limit of Carbon-Containing Impurities in Trichlorosilane]

Sample B which contained 0.1 ppmw of each of supposed impurities and which was for trichlorosilane GC analysis was prepared as a highly purified trichlorosilane, and analyzed under the same conditions as described above.

Figure 4:
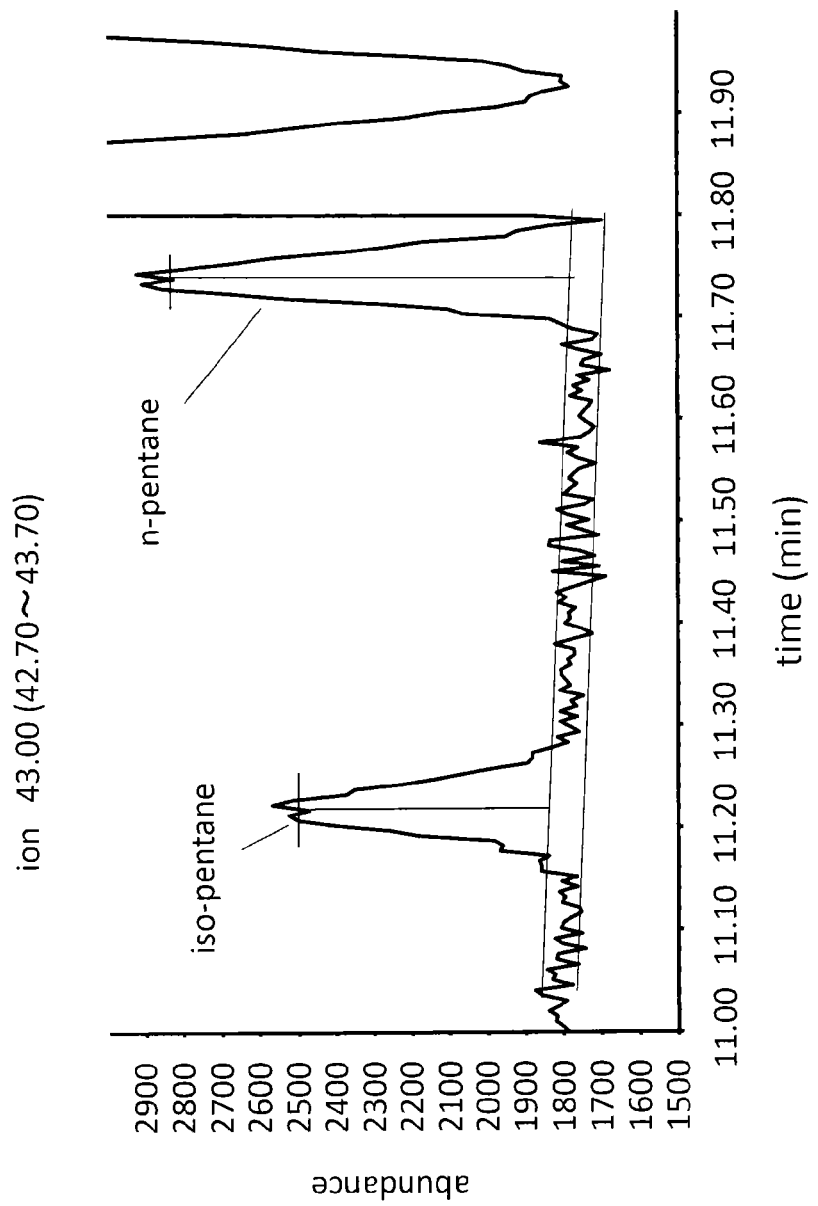
FIG. 4 is a chart (measurement chart of mass number of 43) obtained by GC/MS-SIM analysis of Sample B.
Figure 5:
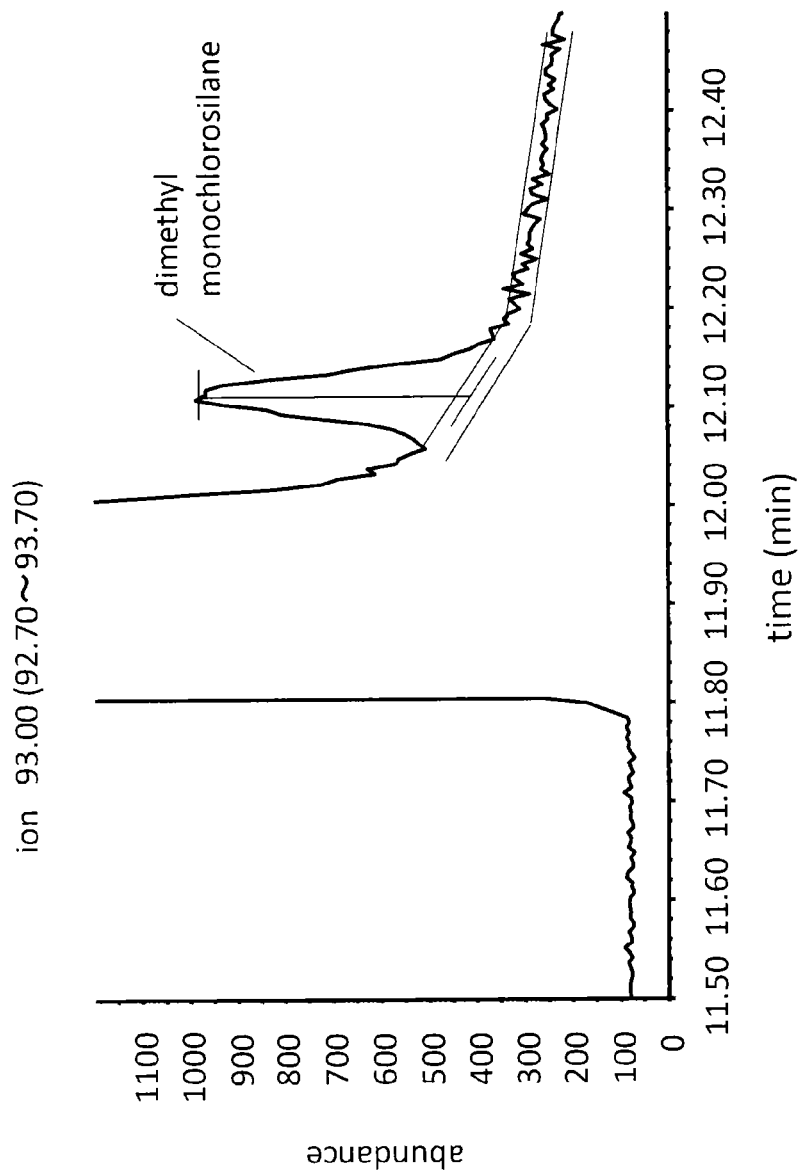
FIG. 5 is a chart (measurement chart of mass number of 93) obtained by GC/MS-SIM analysis of Sample B.
Figure 6:
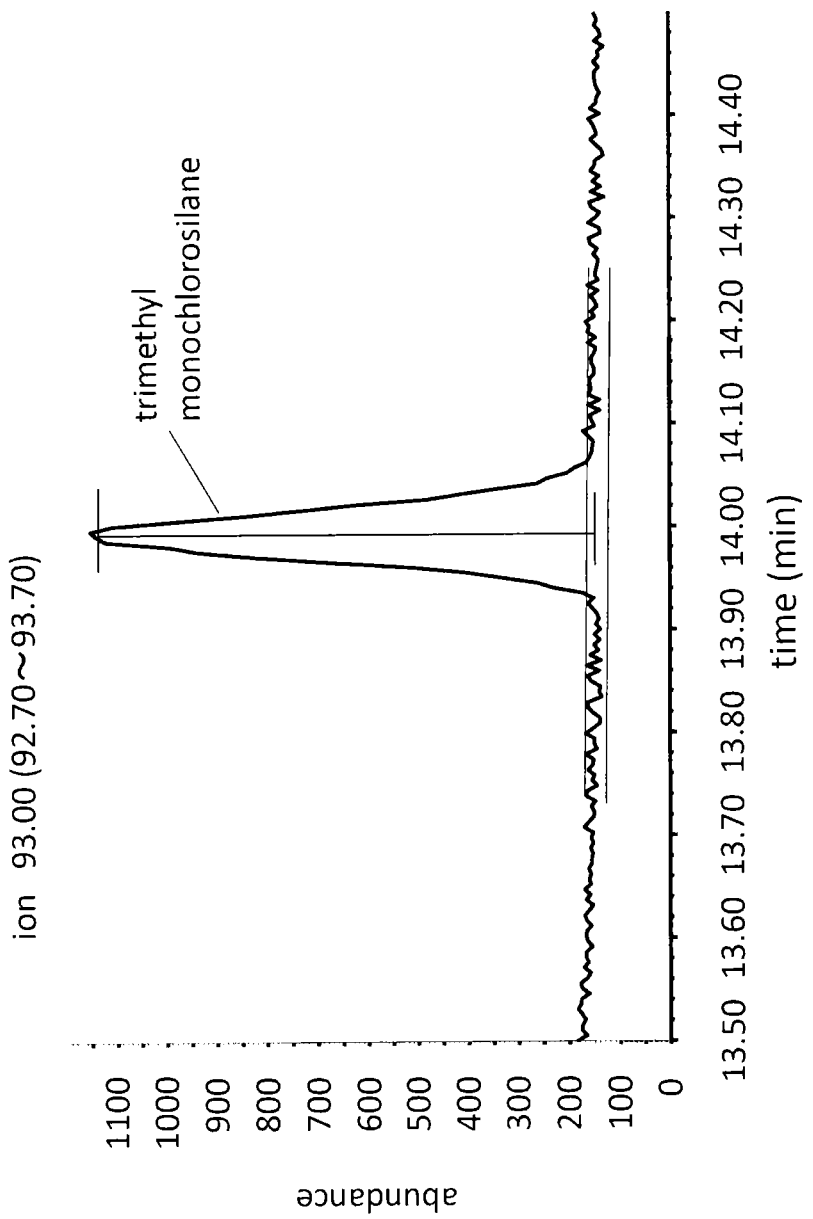
FIG. 6 is a chart (measurement chart of mass number of 93) obtained by GC/MS-SIM analysis of Sample B.
Figure 7:
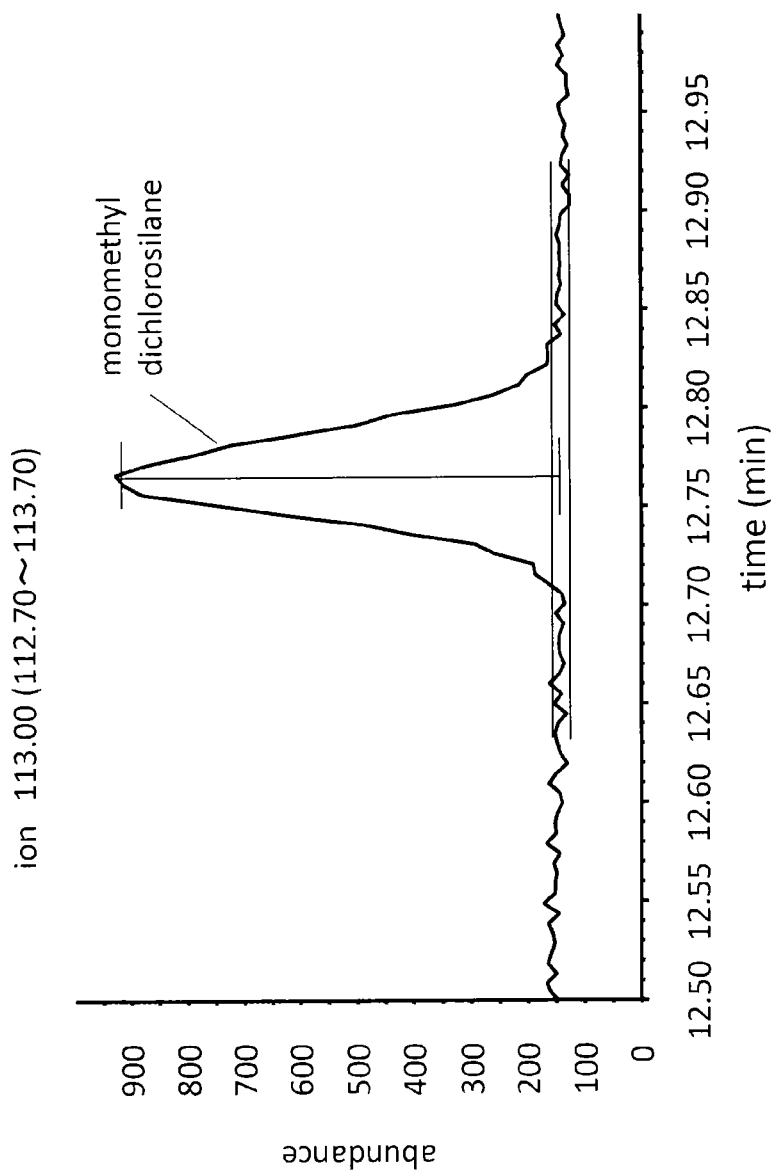
FIG. 7 is a chart (measurement chart of mass number of 113) obtained by GC/MS-SIM analysis of Sample B.
Figure 8:
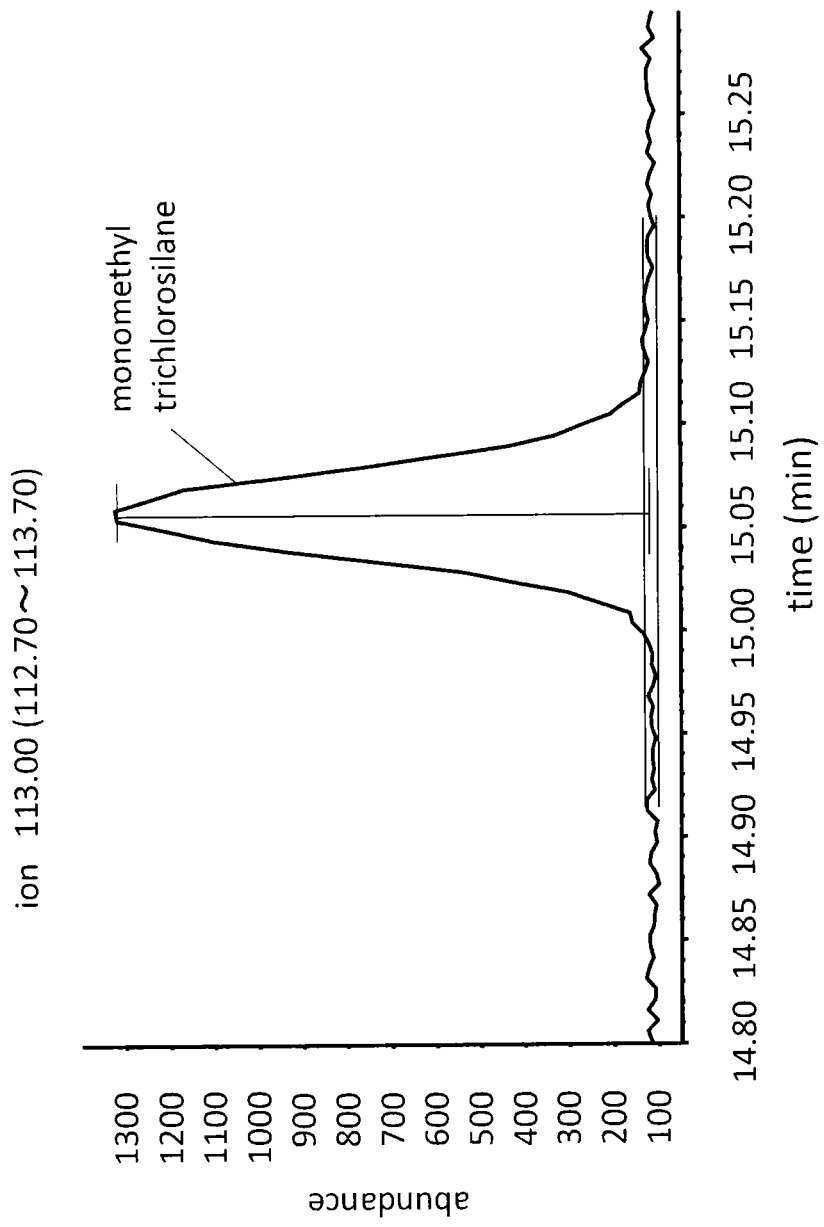
FIG. 8 is a chart (measurement chart of mass number of 113) obtained by GC/MS-SIM analysis of Sample B.
Figure 9:
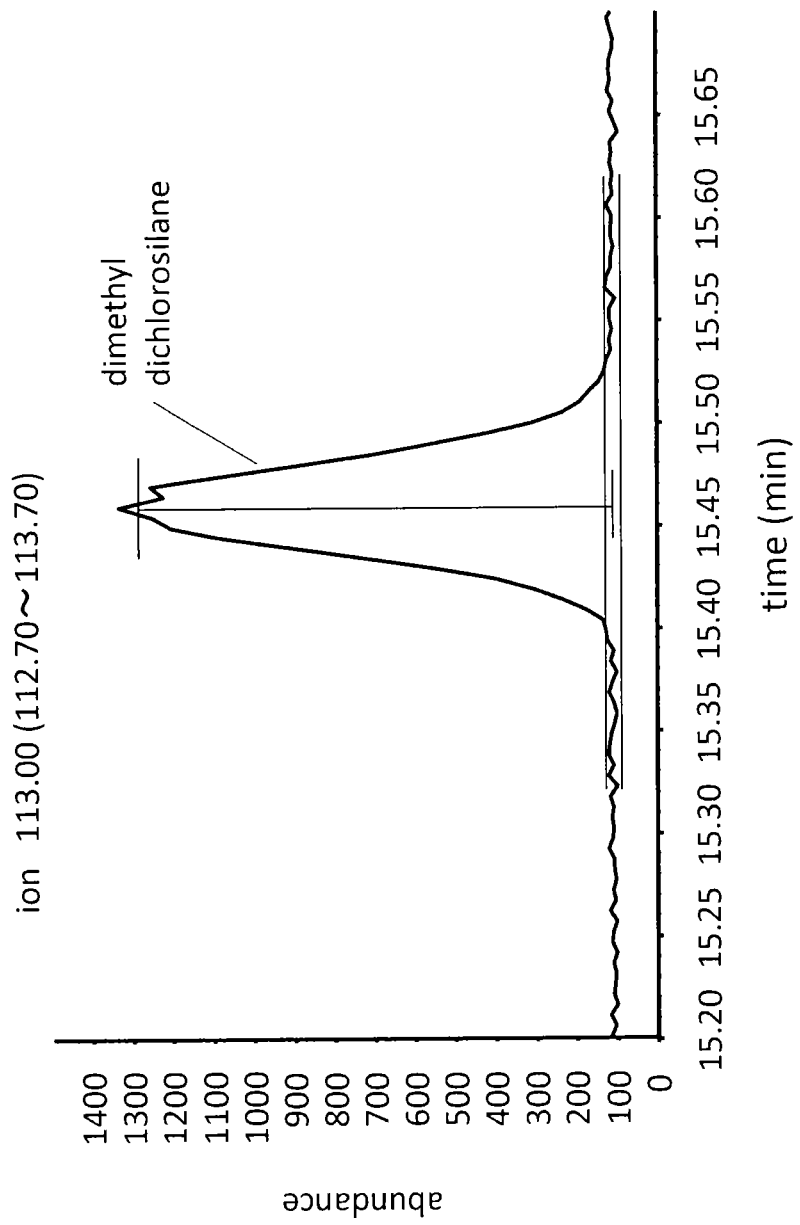
FIG. 9 is a chart (measurement chart of mass number of 113) obtained by GC/MS-SIM analysis of Sample B.

Charts obtained by the GC/MS-SIM analysis are shown in FIGS. 4 to 9. FIG. 4 is a measurement chart of mass number of 43, FIGS. 5 and 6 are measurement charts of mass number of 93, and FIGS. 7 to 9 are measurement charts of mass number of 113. From these charts, the width of base line noise and the height of peak abundance were determined, and further the measurement limit was determined. Then, the detection limit of each component was determined. The results are shown below. The detection limit (SN2) was determined by the following equation.

[$SN2$]=2×(the width (mm) of base line noise)×(0.1 ppmw/the height (mm) of peak abundance)

iso-pentane: SN2=2(3.5 mm)×(0.1 ppmw/28 mm)=<0.03 ppmw
n-pentane: SN2=2(3.5 mm)×(0.1 ppmw/43 mm)=<0.02 ppmw
dichloromonochlorosilane: SN2=2(2.0 mm)×(0.1 ppmw/26 mm)=<0.02 ppmw
trimethylmonochlorosilane: SN2=2(2.0 mm)×(0.1 ppmw/46 mm)=<0.01 ppmw
monomethyldichlorosilane: SN2=2(1.5 mm)×(0.1 ppmw/42 mm)=<0.01 ppmw
monomethyltrichlorosilane: SN2=2(1.0 mm)×(0.1 ppmw/50 mm)=<0.01 ppmw
dimethyldichlorosilane: SN2=2(1.5 mm)×(0.1 ppmw/45 mm)=<0.01 ppmw These results reveal that use of GC/MS-SIM method enables the analysis of carbon-containing impurities with very high sensitivity.

[Comparison of GC/MS-SIM Method and GC-FID Method]

Three kinds of trichlorosilane samples (Samples 1-3) different from each other in the distillation accuracy were prepared, and analyzed by GC/MS-SIM method and GC-FID method to compare with each other in the detection sensitivity of peaks caused by impurities. The analysis was performed under the conditions as described above, and each component was quantified by an absolute calibration curve method.

Figure 10:
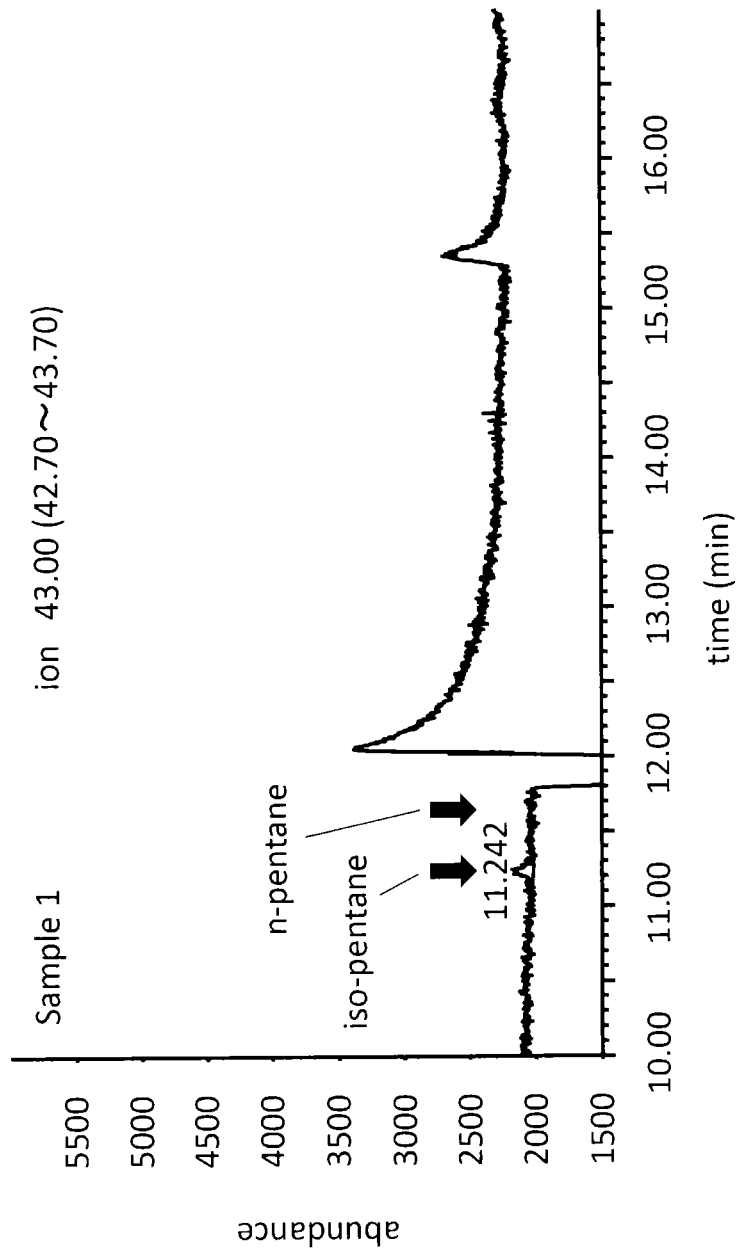
FIG. 10 is a chart (mass number of 43) obtained by GC/MS-SIM analysis of Sample 1.
Figure 11:
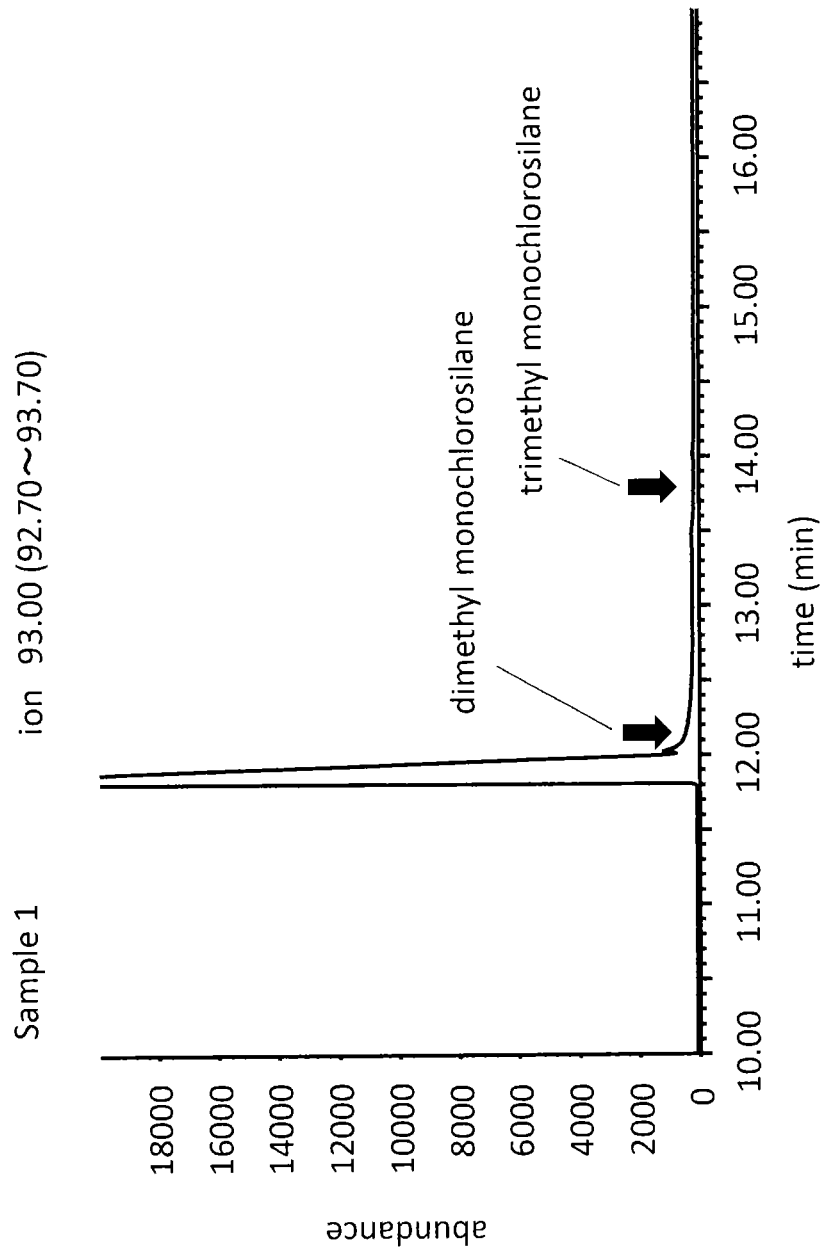
FIG. 11 is a chart (mass number of 93) obtained by GC/MS-SIM analysis of Sample 1.
Figure 12:
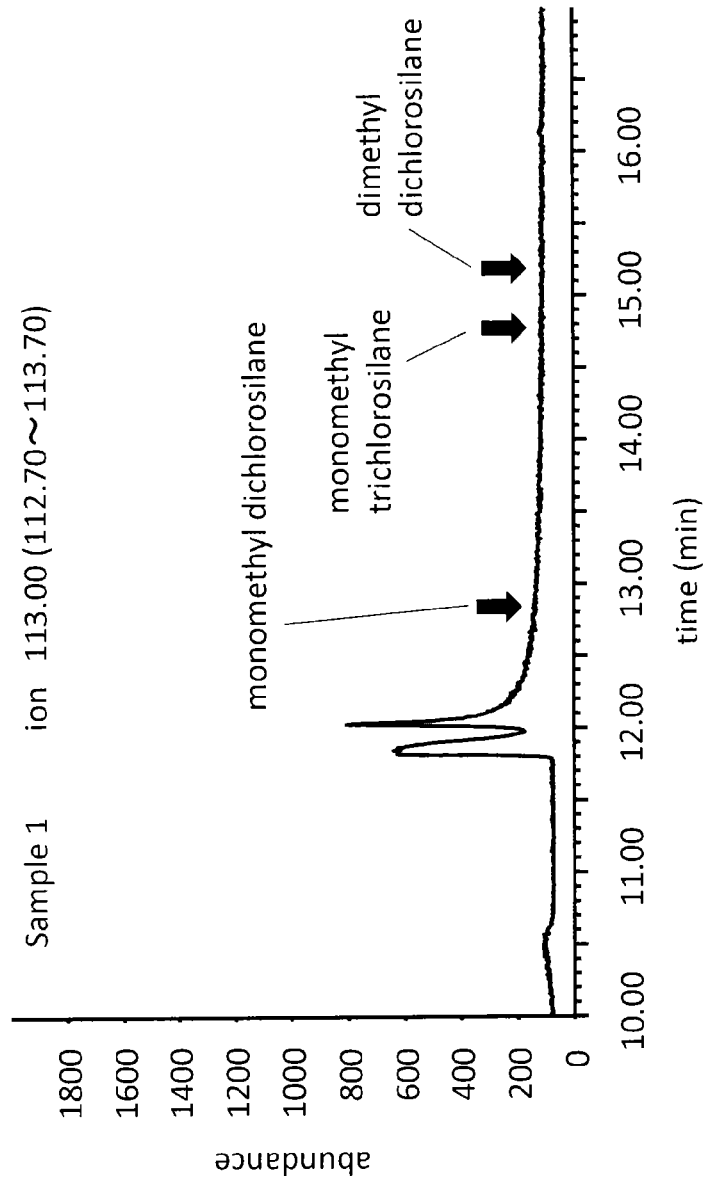
FIG. 12 is a chart (mass number of 113) obtained by GC/MS-SIM analysis of Sample 1.
Figure 13:
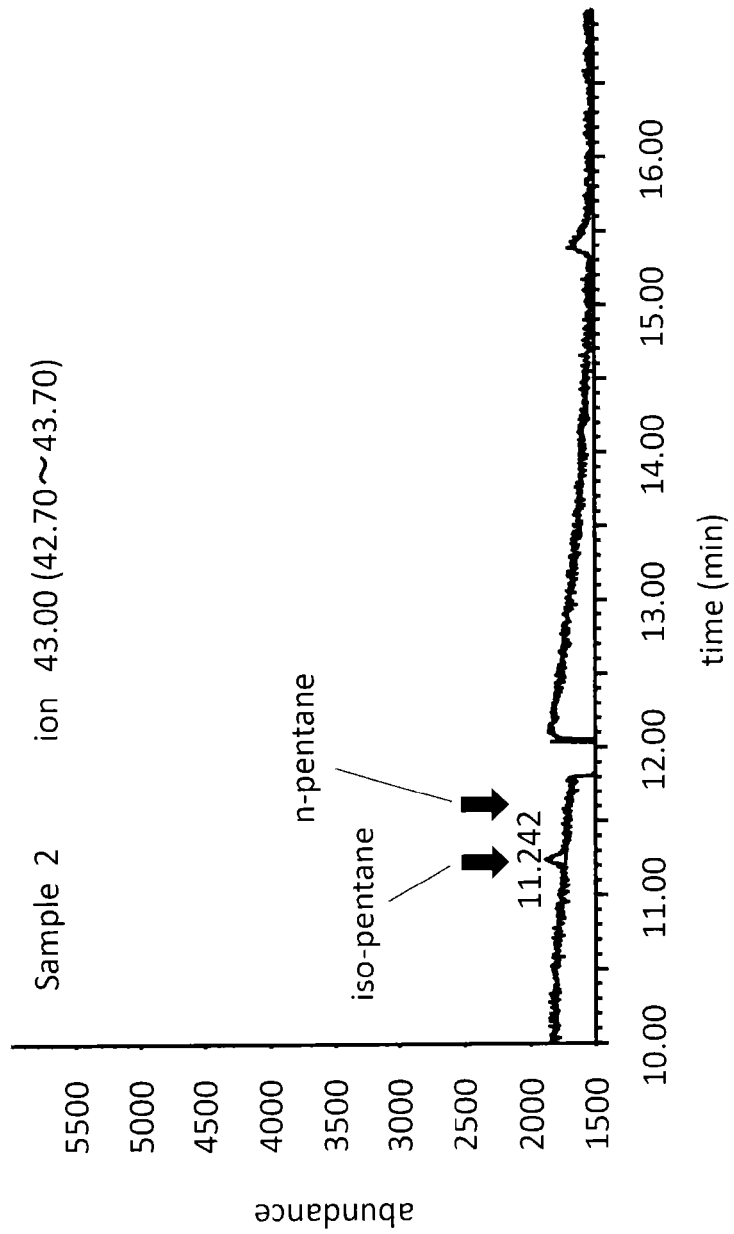
FIG. 13 is a chart (mass number of 43) obtained by GC/MS-SIM analysis of Sample 2.
Figure 14:
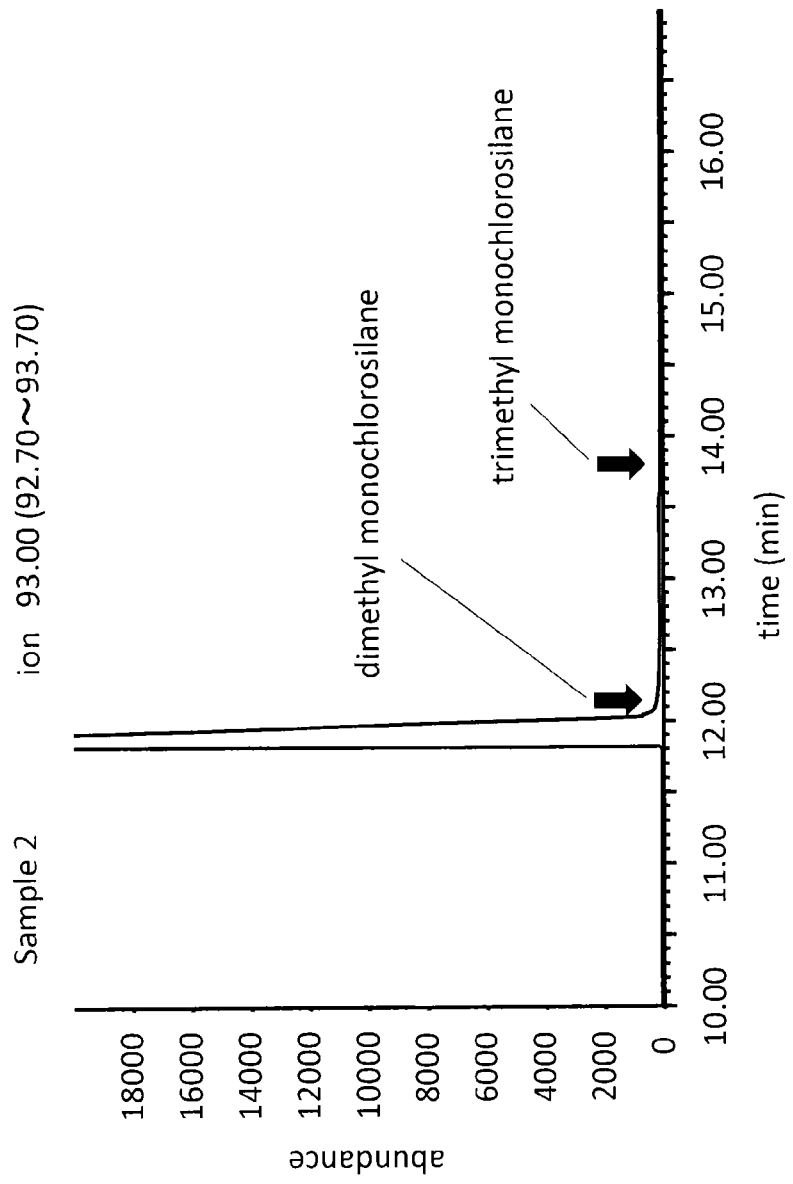
FIG. 14 is a chart (mass number of 93) obtained by GC/MS-SIM analysis of Sample 2.
Figure 15:
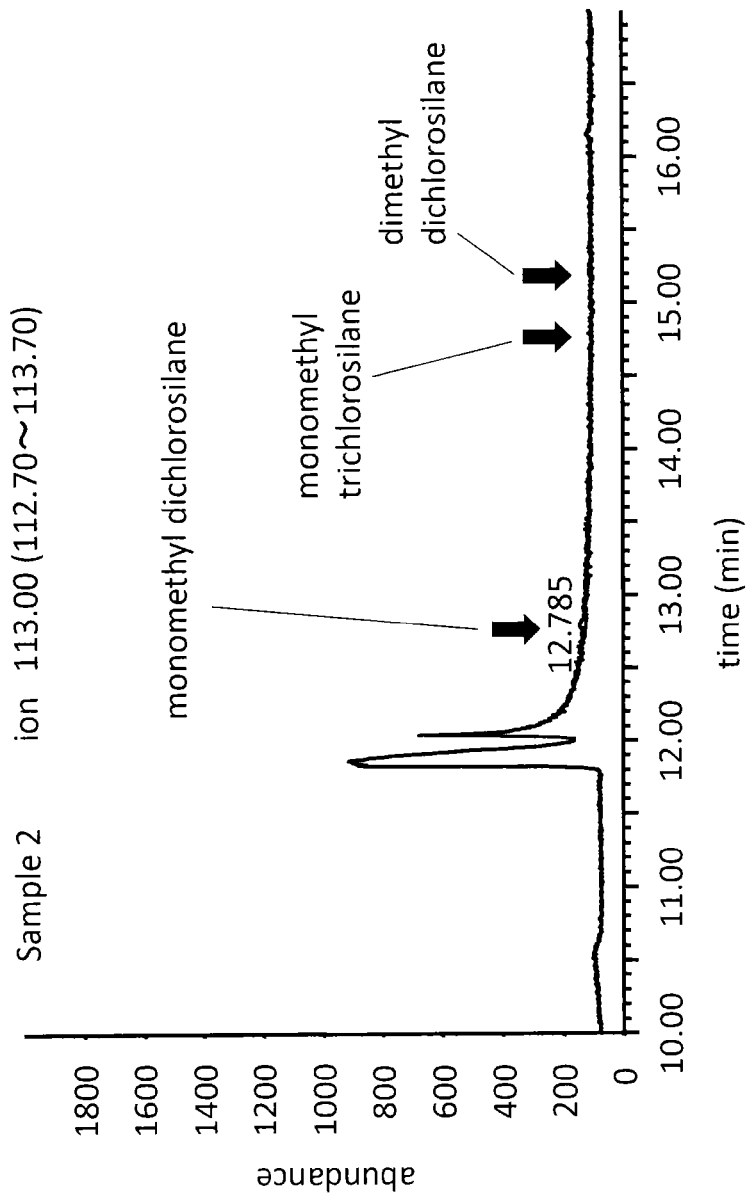
FIG. 15 is a chart (mass number of 113) obtained by GC/MS-SIM analysis of Sample 2.
Figure 16:
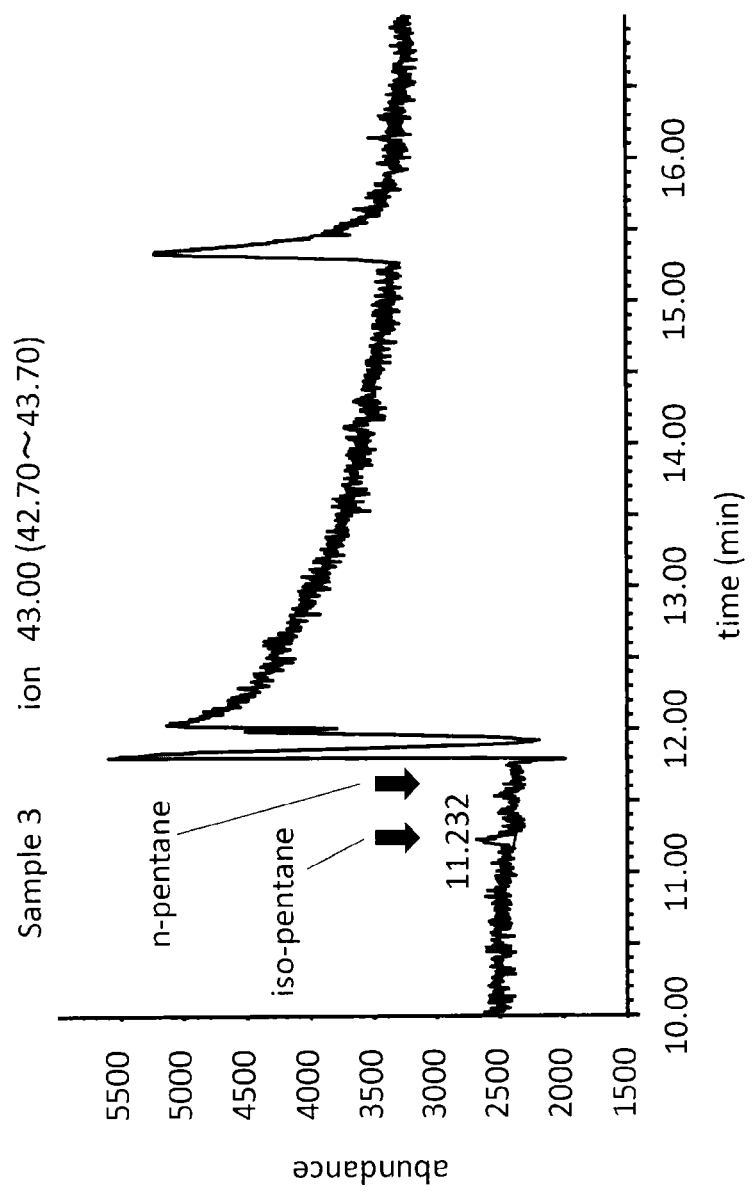
FIG. 16 is a chart (mass number of 43) obtained by GC/MS-SIM analysis of Sample 3.
Figure 17:
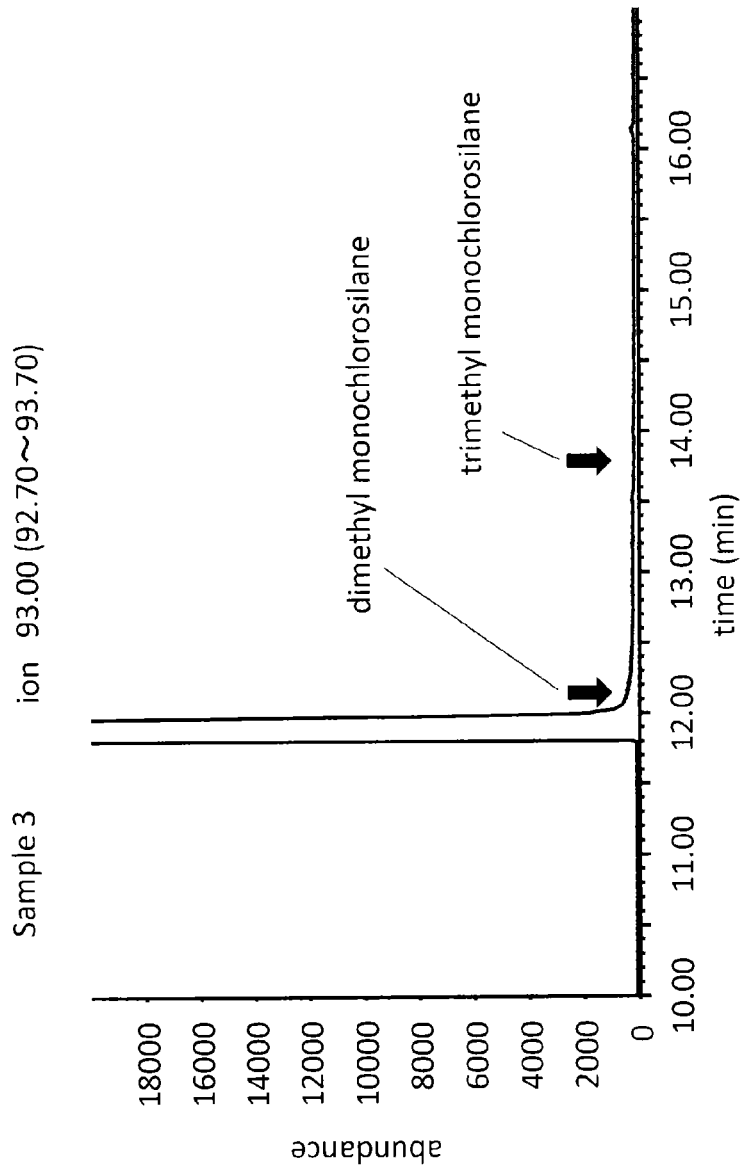
FIG. 17 is a chart (mass number of 93) obtained by GC/MS-SIM analysis of Sample 3.
Figure 18:
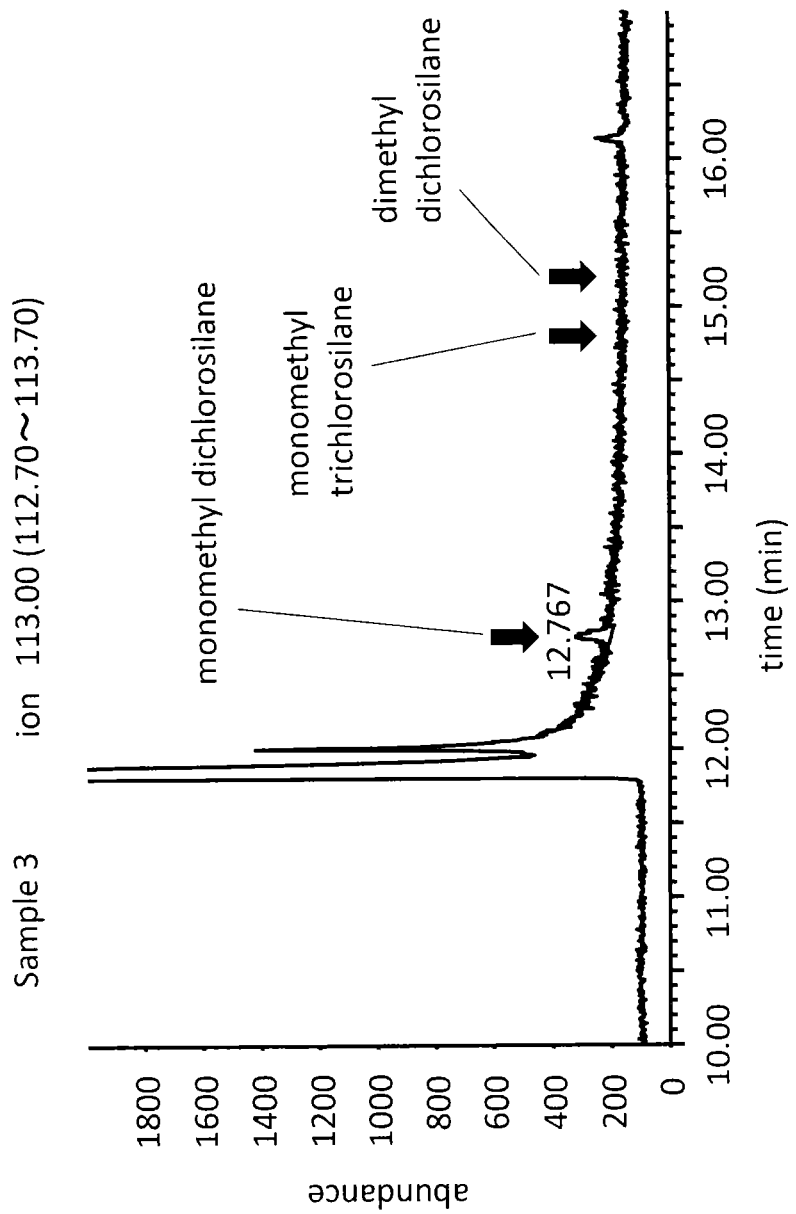
FIG. 18 is a chart (mass number of 113) obtained by GC/MS-SIM analysis of Sample 3.

FIGS. 10 to 12 are charts obtained by the GC/MS-SIM analysis of Sample 1; FIGS. 13 to 15 are charts obtained by the GC/MS-SIM analysis of Sample 2; and FIGS. 16 to 18 are charts obtained by the GC/MS-SIM analysis of Sample 3. The quantitative analysis results obtained from these charts are summarized in Table 1 (the concentration is ppmw).

TABLE 1

| | Detection method | Analyzed sample | Concentration of methyl-dichlorosilane | Concentration of hydrocarbon |
|---|---|---|---|---|
| Example 1 | GC/MS-SIM | Sample 1 | <0.01 | 0.05 |
| Comparative Example A1 | GC/MS-SIM | Sample 2 | 0.01 | 0.06 |

TABLE 1-continued

| | Detection method | Analyzed sample | Concentration of methyl-dichlorosilane | Concentration of hydrocarbon |
|---|---|---|---|---|
| Comparative Example A2 | GC/MS-SIM | Sample 3 | 0.08 | 0.03 |
| Comparative Example B1 | GC-FID | Sample 1 | <0.1 | <0.5 |
| Comparative Example B2 | GC-FID | Sample 2 | <0.1 | <0.5 |
| Comparative Example B3 | GC-FID | Sample 3 | <0.1 | <0.5 |

In these analyses, only methyldichlorosilane as alkylchlorosilanes was detected to be a significant impurity. Only isopentane as hydrocarbons was also detected to be a significant impurity.

GC-FID method was not able to detect any of methyldichlorosilane and hydrocarbons for all samples, but GC/MS-SIM method was able to detect carbon-containing impurities with high sensitivity, except that methyldichlorosilane of Sample 1 was lower than the detection limit (<0.01 ppmw).

Figure 19:
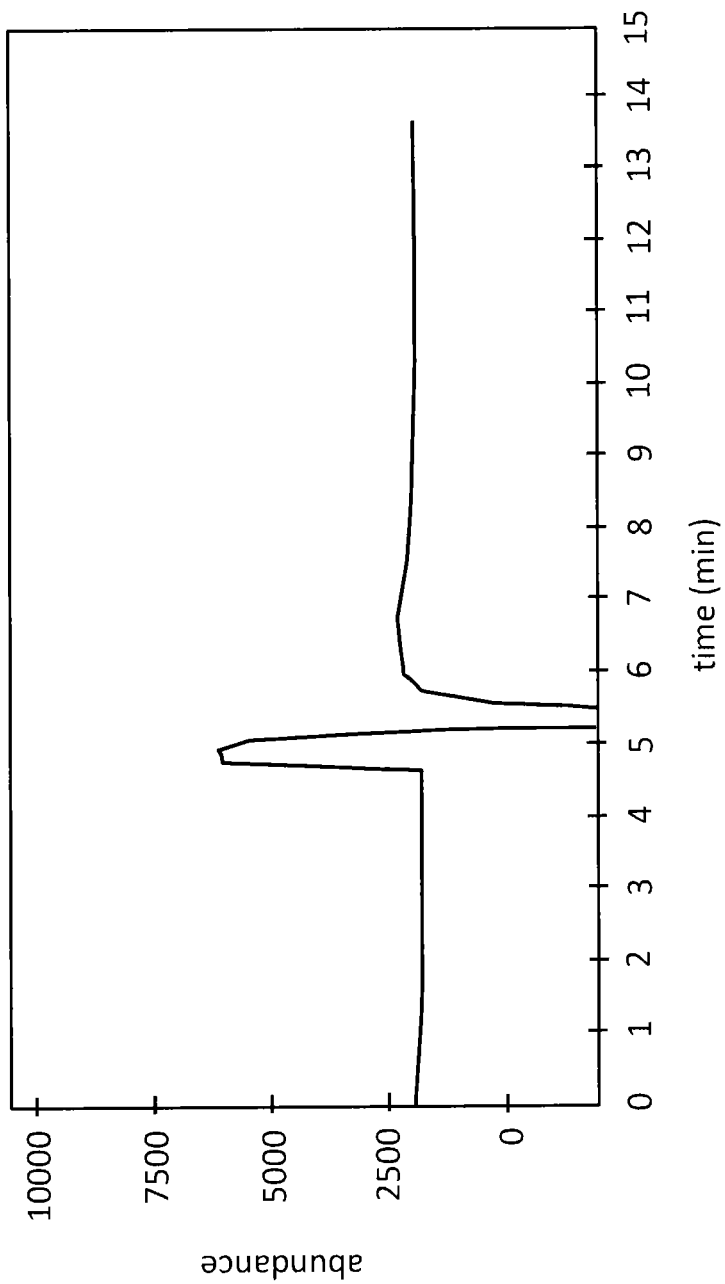
FIG. 19 is a chart obtained by GC-FID analysis of Sample 2.

FIG. 19 is a chart obtained by the GC-FID analysis of Sample 2. When this chart is compared with charts of FIGS. 13 to 15 obtained by the GC/MS-SIM analysis, it is revealed that the GC-FID analysis was not able to detect the peaks (methyldichlorosilane and isopentane) which were able to be detected by the GC/MS-SIM analysis.

Figure 20:
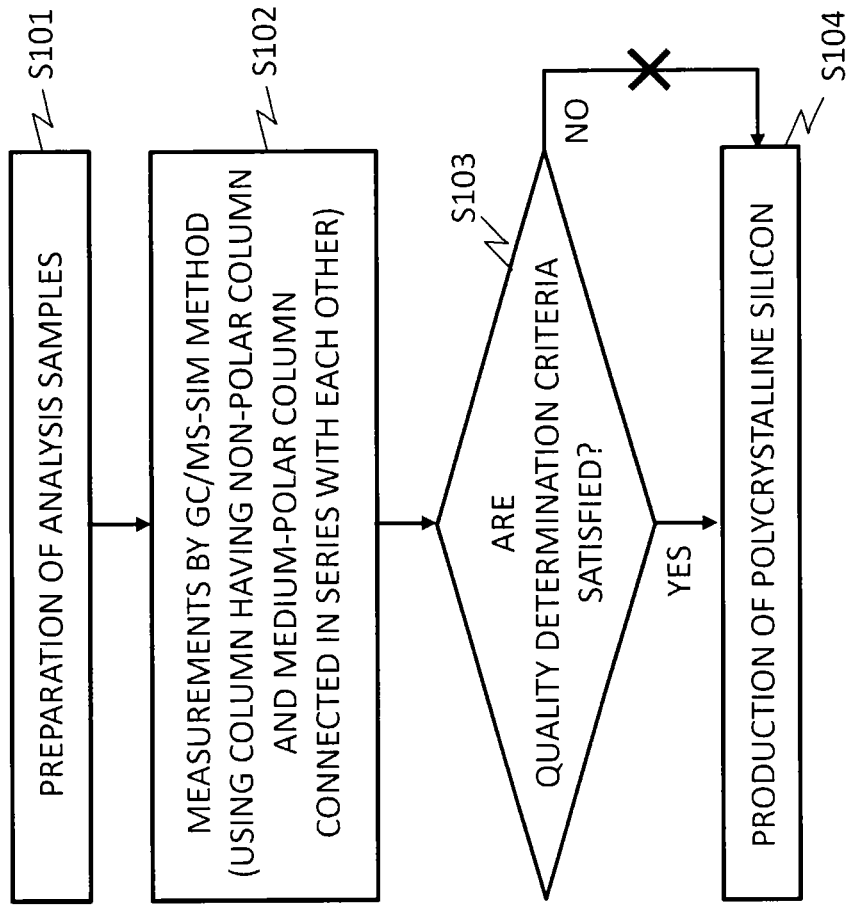
FIG. 20 is a flow scheme of a method for producing a polycrystalline silicon according to the present invention.

FIG. 20 is a flow scheme of a method for producing a polycrystalline silicon according to the present invention. This example is a flow scheme of the production of a polycrystalline silicon using Sample 1 described above as a raw material according to Siemens method.

First, Sample 1 which is trichlorosilane is prepared (S101), and the content of carbon-containing impurities in Sample 1 is analyzed by GC/MS-SIM method (S102). A quality determination is made on the basis of the analysis results (S103) and, in case that the sample is determined to be a good material (S103: Yes), the sample is used as a raw material for producing a high-purity polycrystalline silicon by CVD method (S104). On the other hand, in case that the sample is determined to be a bad material (S103: No), the sample is not used as the raw material for producing a polycrystalline silicon. As described above, the analysis of the impurities by GC/MS-SIM method was performed using, as a separation column, a column having a non-polar column and a medium-polar column connected in series with each other.

The criteria of the above quality determination were that methylsilanes as the carbon-containing impurities were 0.01 ppmw or lower, and hydrocarbons as the carbon-containing impurities were 0.05 ppmw or lower. Sample 1 was therefore determined to be a good material. Thus, a polycrystalline silicon was produced using Sample 1 by Siemens method (refer to Patent Literature 1).

A polycrystalline silicon was produced according to the steps described above, and the concentration of carbon in the produced polycrystalline silicon was analyzed by a cryogenic FT-IR method (using BRUKER Optics Corporation, FT-IR, VERTEX80V, liquid nitrogen) to be a low concentration and less than 0.05 ppma.

INDUSTRIAL APPLICABILITY

As described herein above, according to the method for producing a polycrystalline silicon of the present invention, chlorosilanes containing carbon-containing impurities of which content exceeds the quality determination criteria are excluded from the raw material, and the higher purification of a polycrystalline silicon can be therefore achieved.

Further, there is also an advantage that both of the separation of chlorosilanes and hydrocarbons and the separation of chlorosilanes and methylsilanes can be simultaneously performed according to GC/MS-SIM method by using, as a separation column, a column having a non-polar column and a medium-polar column connected in series with each other.

The invention claimed is:

1. A method for producing a high-purity polycrystalline silicon from chlorosilane by CVD, comprising:
   performing a quality determination on a trichlorosilane raw material by analyzing a content of carbon-containing impurities in the trichlorosilane by gas chromatography/mass spectrometry-selected ion monitoring (GC/MS-SIM), the carbon-containing impurities comprising methyldichlorosilane and isopentane, and
   setting trichlorosilane satisfying conditions, which are quality determination criteria, based on permissible values of the content of carbon-containing impurities, wherein the permissible values are provided on the basis of a permissible value of the content of carbon in an objective polycrystalline silicon.

2. The method for producing a high-purity polycrystalline silicon according to claim 1, wherein the carbon-containing impurities analyzed by the GC/MS-SIM are methyldichlorosilane and isopentane.

3. The method for producing a high-purity polycrystalline silicon according to claim 2, wherein the quality determination criteria are that methysilanes as the carbon-containing impurities are 0.01 ppmw or lower, and hydrocarbons as the carbon-containing impurities are 0.05 ppmw or lower.

4. The method for producing a high-purity polycrystalline silicon according to claim 2, wherein the analysis of the carbon-containing impurities by the GC/MS-SIM separates the components using, as the separation column, a column comprising a non-polar column and a medium-polar column connected in series with each other.

5. The method for producing a high-purity polycrystalline silicon according to claim 1, wherein the quality determination criteria are that methylsilanes as the carbon-containing impurities are 0.01 ppmw or lower, and hydrocarbons as the carbon-containing impurities are 0.05 ppmw or lower.

6. The method for producing a high-purity polycrystalline silicon according to claim 1, wherein the analysis of the carbon-containing impurities by the GC/MS-SIM separates the components using, as the separation column, a column comprising a non-polar column and a medium-polar column connected in series with each other.

* * * * *